United States Patent
Schwarz et al.

(10) Patent No.: US 6,913,613 B2
(45) Date of Patent: Jul. 5, 2005

(54) SURGICAL INSTRUMENT FOR MINIMALLY INVASIVE SURGICAL INTERVENTIONS

(75) Inventors: Knut M. Schwarz, Tübingen (DE); Marc O. Schurr, Tübingen (DE); Gerhard F. Buesz, Tübingen (DE)

(73) Assignee: Tuebingen Scientific Surgical Products oHG, Tübingen (DE)

( * ) Notice: Subject to any disclaimer, the term of this patent is extended or adjusted under 35 U.S.C. 154(b) by 0 days.

(21) Appl. No.: 10/345,019

(22) Filed: Jan. 15, 2003

(65) Prior Publication Data

US 2003/0109898 A1 Jun. 12, 2003

Related U.S. Application Data

(63) Continuation of application No. 10/333,517, filed as application No. PCT/EP00/08802 on Sep. 8, 2000.

(30) Foreign Application Priority Data

| Sep. 9, 1999 | (DE) | 199 43 018 |
| Jul. 25, 2000 | (DE) | 100 36 108 |

(51) Int. Cl.$^7$ .............................. A61B 17/28
(52) U.S. Cl. ................................ 606/206; 604/22
(58) Field of Search ................. 606/205, 206, 606/207, 110, 111, 112, 113, 158, 160, 170, 174, 51, 52; 604/19, 20, 27, 28, 93, 22, 164; 600/104, 564

(56) References Cited

U.S. PATENT DOCUMENTS

| 5,209,747 | A | * | 5/1993 | Knoepfler .................... 606/16 |
| 5,254,130 | A | * | 10/1993 | Poncet et al. ............... 606/206 |
| 5,281,220 | A | | 1/1994 | Blake, III .................... 606/46 |
| 5,339,799 | A | * | 8/1994 | Kami et al. ................. 600/117 |
| 5,549,637 | A | * | 8/1996 | Crainich .................... 606/207 |
| 5,626,607 | A | * | 5/1997 | Malecki et al. ............. 606/205 |
| 5,827,323 | A | | 10/1998 | Klieman et al. ............ 606/205 |
| 5,836,960 | A | | 11/1998 | Kolesa et al. .............. 606/170 |
| 5,935,097 | A | * | 8/1999 | Metsch et al. ............... 604/27 |
| 6,364,846 | B1 | | 4/2002 | Nakamura .................. 600/564 |

FOREIGN PATENT DOCUMENTS

| DE | 196 47 761 C1 | 1/1998 | .......... G02B/23/24 |
| DE | 198 35 445 A1 | 3/1999 | .......... A61B/10/00 |
| EP | 0 630 614 A1 | 12/1994 | ......... A61B/17/068 |

* cited by examiner

*Primary Examiner*—Julian W. Woo
*Assistant Examiner*—Victor Nguyen
(74) *Attorney, Agent, or Firm*—Cohen, Pontani, Lieberman & Pavane

(57) ABSTRACT

A surgical instrument for minimally invasive surgery includes a hollow shank with an actuating device arranged at the one end thereof and a bendable instrument tip arranged at the other end. The instrument tip is bendable toward the shank and carries a mouth part. The surgical instrument also includes a gear mechanism which transforms at least a movement of said actuating device by an operator into a rotation of said mouth part according to a predetermined transmission ratio in relation to the actuating movement.

14 Claims, 15 Drawing Sheets

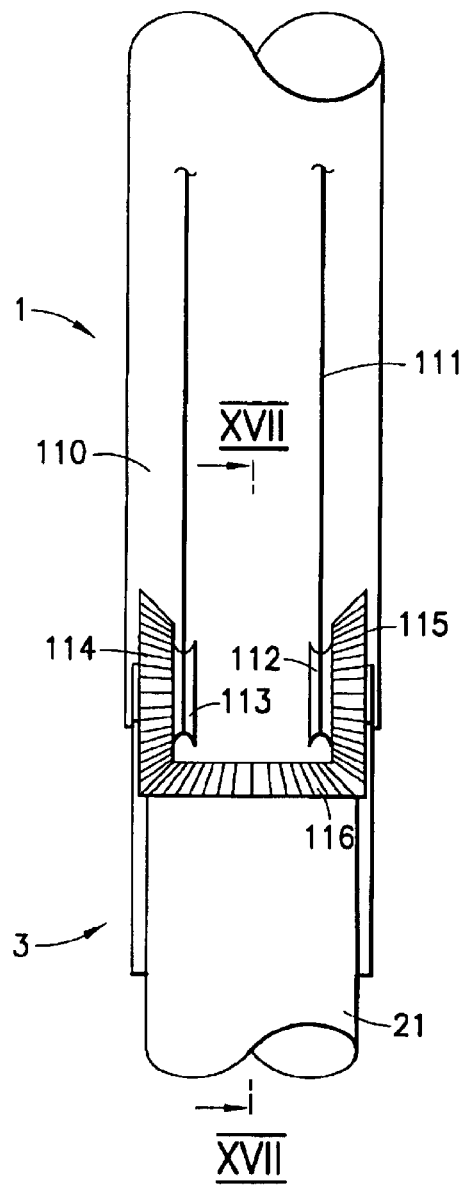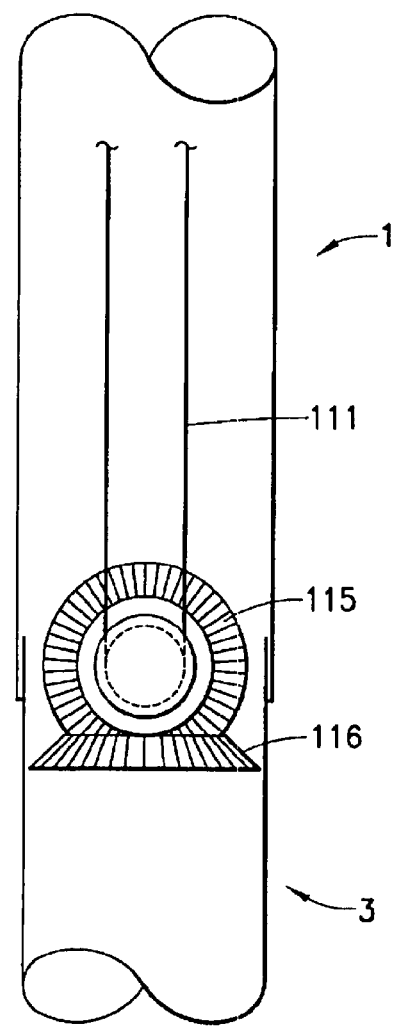
FIG.16
FIG.17

SURGICAL INSTRUMENT FOR MINIMALLY INVASIVE SURGICAL INTERVENTIONS

RELATED APPLICATIONS

The present application is a continuation application of U.S. application Ser. No. 10/333,517 now abandoned, filed Jan. 15, 2003 which is a U.S. National Stage application of PCT application Ser. No. PCT/EP00/08802, filed Sep. 8, 2000, which claims priority on foreign Applications filed in Germany, No. 199 43 018.7, on Sep. 9, 1999, and No. 100 36 108.0, on Jul. 25, 2000.

BACKGROUND OF THE INVENTION

1. Field of the Invention

The present invention relates to a surgical instrument or use in minimally invasive surgical techniques.

2. Description of the Related Art

Minimally invasive surgery lowers morbidity rates and shortens recovery periods and thus also causes substantially lower process and overall treatment costs for a patient compared to open surgery. Most recent developments in the field of minimally invasive surgery have been directed to instruments for complex operations such as, for example, in cardiosurgery, thereby reducing the risks and strains for the patient even in complex operations and reducing costs for private and legal insurances. It is expected that the spectrum of applications of the minimally invasive surgical technique shall not only be extended but also that the instruments used for this purpose shall additionally become cheaper despite the ever more improved surgical techniques.

U.S. Pat. No. 5,254,130 discloses a surgical device for minimally invasive surgery including a tubular or shank-like housing having an axially extending shank bore. A first oblong part includes an elastic preshaped, i.e., curved, material which extends through the shank bore and includes a proximal end and a distal end. When the distal end is extended out of the longitudinal bore, it adopts a first shape corresponding to the preshaping, i.e., the curve. When the distal end is retracted back into the bore, it adopts a second shape corresponding to the shape of the shank bore, i.e., the first part straightens when it is retracted into the bore.

A second oblong part, which also has a proximal end and distal end, is linked to the first part at a parallel distance therefrom. The second part is bent by the first part, when the first part changes from its first to its second shape and vice versa. In addition, the second part is held relatively rotatably about the axis of the first part.

A working head or mouth member is arranged at the distal end of the second oblong part. The working head or mouth member moves along with the second part during the bending or curving movements of the latter and is rotatable about the axis of the first part by the second part. This configuration enables an operator to move the head of the surgical device for instance along a path curved in a plane and then to rotate the working head in a different dimension, for instance about the axis defined by the direction of the curved path.

SUMMARY OF THE INVENTION

It is an object of the invention to provide a generic surgical instrument of high functionality for minimally invasive surgery.

This object is achieved by a surgical instrument having a hollow shank having a proximal end and a distal end, an actuating device arranged at the proximal end, and an instrument tip bendable or pivotal toward the shank which carries a mouth part arranged at the distal end thereof. In accordance with the present invention, a gear mechanism is provided which transforms at least a first movement of the actuating device, preferably triggered by manual rotation of an operator, into a rotation of the mouth part according to a first specific transmission ratio in relation to the first actuating movement. This allows the rotation of the instrument tip, especially the mouth part, up to, for example, 300° despite the relatively limited possibility of movement of a human hand. Higher and lower degrees of rotation are possible depending on the purpose of use by choosing an appropriate transmission ratio. The invention facilitates the realization of complex motions without requiring a "changing of grip" by the user. The force or moment transmission mechanism preferably operatively connects the actuating device to the instrument tip without an expensive and complex sensor technology, e.g., without the electronic detection of actuating movements and the calculation and transmission of movement signals to the instrument tip and/or the drive thereof. This preferred immediacy of the instrument according to the present invention enables an operating surgeon to easily start on the minimally invasive surgery and/or accelerates the learning process in handling the instrument according to the present invention.

The bendable instrument tip may forms a sleeve-like or case-like seat for rotatably supporting the mouth part. The seat itself is supported so that it does not rotate but is swivelable at the distal end of the hollow shank. The gear mechanism transforms a second movement of the actuating device, preferably triggered by a bending of the operator's hand, into a swiveling and/or bending of the seat with respect to the hollow shank. The second movement is transformed according to a second predetermined transmission ratio in relation to the corresponding second actuating movement. The second movement is completely uncoupled from the first actuating movement.

An actuating element movable relative to the actuating device may further be provided which is actuatable independent of the relative position of the actuating device to the hollow shank for opening and closing the mouth part by the operator's hand. The movement of the actuating element is uncoupled from the first and second actuating movement.

Other objects and features of the present invention will become apparent from the following detailed description considered in conjunction with the accompanying drawings. It is to be understood, however, that the drawings are designed solely for purposes of illustration and not as a definition of the limits of the invention, for which reference should be made to the appended claims. It should be further understood that the drawings are not necessarily drawn to scale and that, unless otherwise indicated, they are merely intended to conceptually illustrate the structures and procedures described herein.

BRIEF DESCRIPTION OF THE DRAWINGS

In the drawings, wherein like reference characters denote similar elements throughout the several views:

FIG. 16 is a schematic side view of a connecting portion of an instrument tip to a hollow shank according to yet another embodiment of the present invention; and FIG. 17 is a sectional view of the connection portion of FIG. 16 along line XVII—XVII.

DETAILED DESCRIPTION OF THE PRESENTLY PREFERRED EMBODIMENTS

Figure 1:
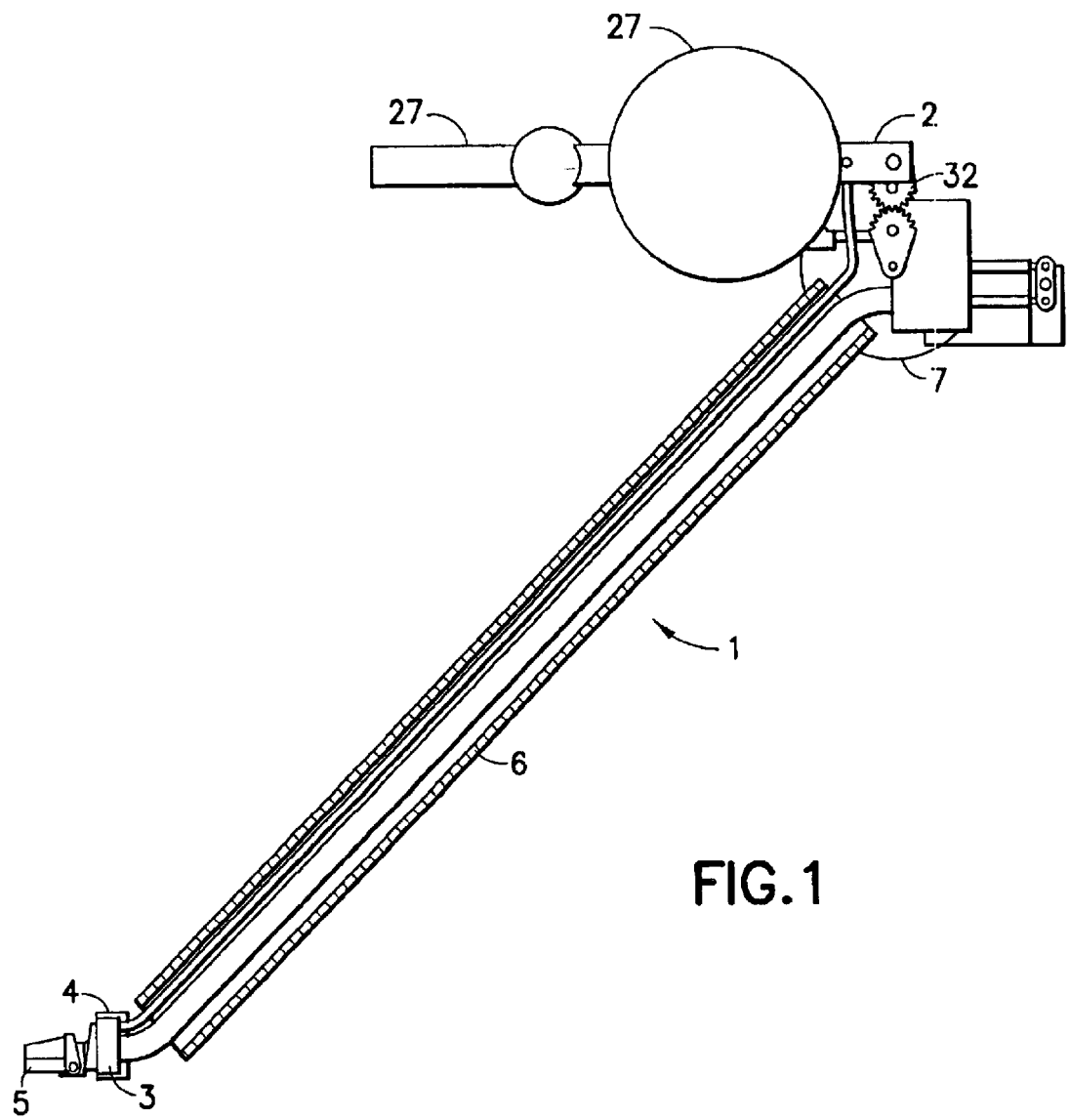
FIG. 1 is a side view of a surgical instrument for minimally invasive surgery according to an embodiment of the present invention.

As shown in FIG. 1, a surgical instrument according to a first embodiment of the present invention includes a hollow shank 1 preferably made of a deflection-resistant and torsion-resistant material or structure. An actuating device 2 is arranged at a first axial end portion of the hollow shank 1, hereinafter referred to as the proximal end portion. An instrument tip 3 having a case-like seat 4 for rotatably carrying a mouth part 5 is arranged at the second axial end of the hollow shank 1, hereinafter referred to as the distal end portion, the seat being pivotable toward the proximal end portion of the hollow shank 1. The surgical instrument further includes a force and/or torque transmission mechanism (gear mechanism) through which both the seat 4 and the mouth part 5 are mechanically coupled with the actuating device 2 for the independent actuation thereof.

Figure 3:
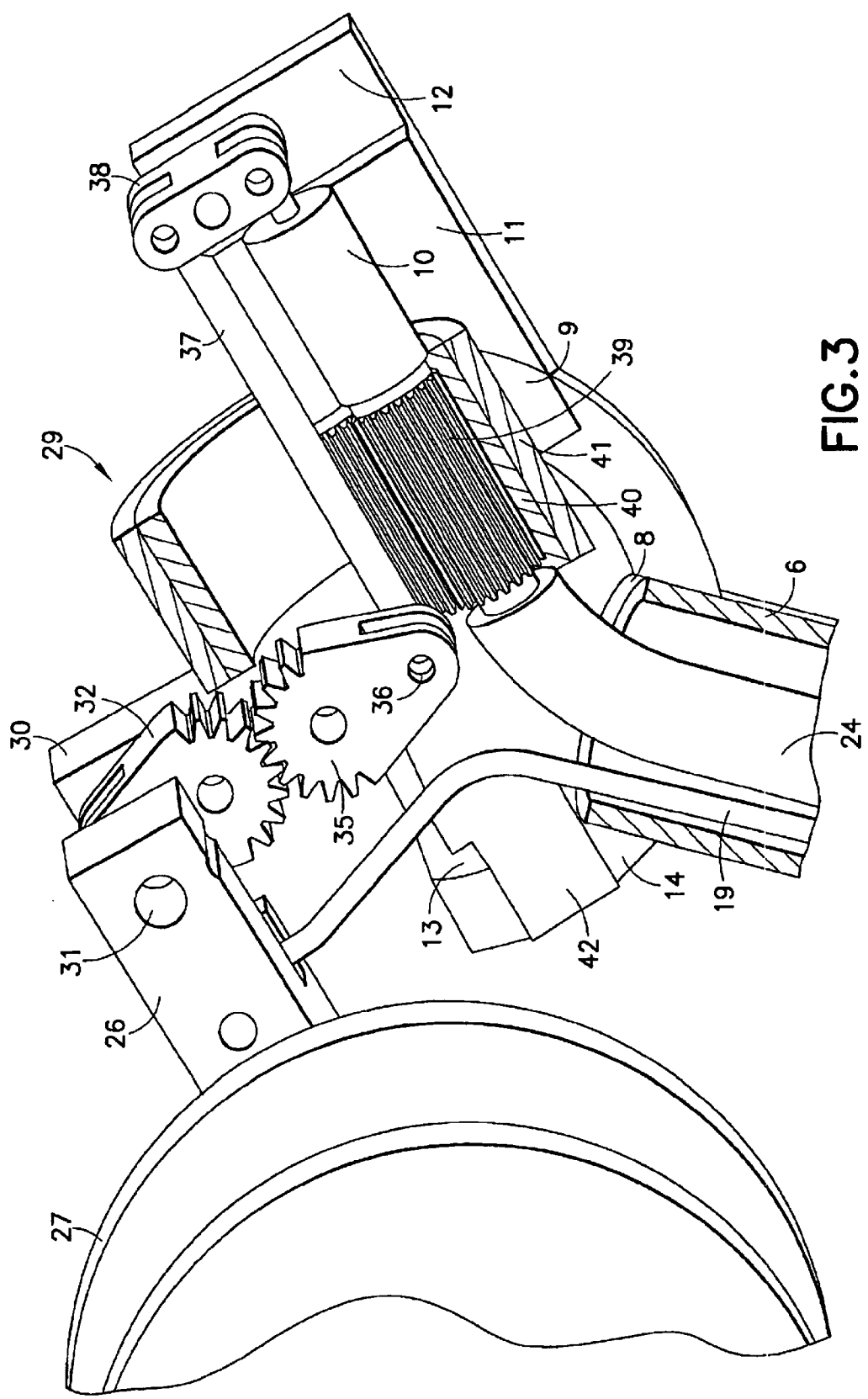
FIG. 3 is a partial sectional side view of the actuating device of FIG. 2.

The hollow shank 1 is formed by an oblong substantially deflection-resistant tubular piece 6 of a non-oxidizing metal which is cut square to a predetermined dimension at its axial ends. Referring also to FIG. 3, a spherical cap 7 is arranged at the proximal end portion of the tubular piece and may be attached to the tubular piece 6, for example, by hard-soldering, welding or screwing. The spherical cap 7 has an inlet bore 8 with a diameter corresponding approximately to the inner diameter of the tubular piece 6. The opening of the inlet bore 8 is axially aligned into the tubular piece 6. The spherical cap 7 further includes an outlet bore 9 of a substantially equal diameter whose central axis is aligned at an angle of between 100° and 150°, preferably 135°, with respect to the central axis of the inlet bore 8.

An extension or base 11 with a longitudinal bore 10 is connected to the outlet bore 9 and is preferably formed integrally with the spherical cap 7 at the outside thereof so that the longitudinal bore 10 opens at a predetermined parallel distance from the central axis of the outlet bore 9. The longitudinal bore 10 has a smaller diameter than that of the outlet bore 9. Moreover, a link point 12 is formed at the free end portion of the extension 11 for movably linking levers and/or rods of a force transmission mechanism, as will be described below.

A segment of the spherical cap 7 is removed at a portion of the spherical cap 7 excluding the inlet and outlet bores 8, 9. The removed segment provides a free access 13 to an interior of the spherical cap 7. In the remaining ball segment of the spherical cap 7, a bearing bore 14 is formed between the inlet opening 8 and the free access 13. The bearing bore is arranged in axial alignment with the outlet bore 9 but has a smaller diameter compared to the outlet bore 9 which corresponds approximately to that of the longitudinal bore 10.

Figure 5:
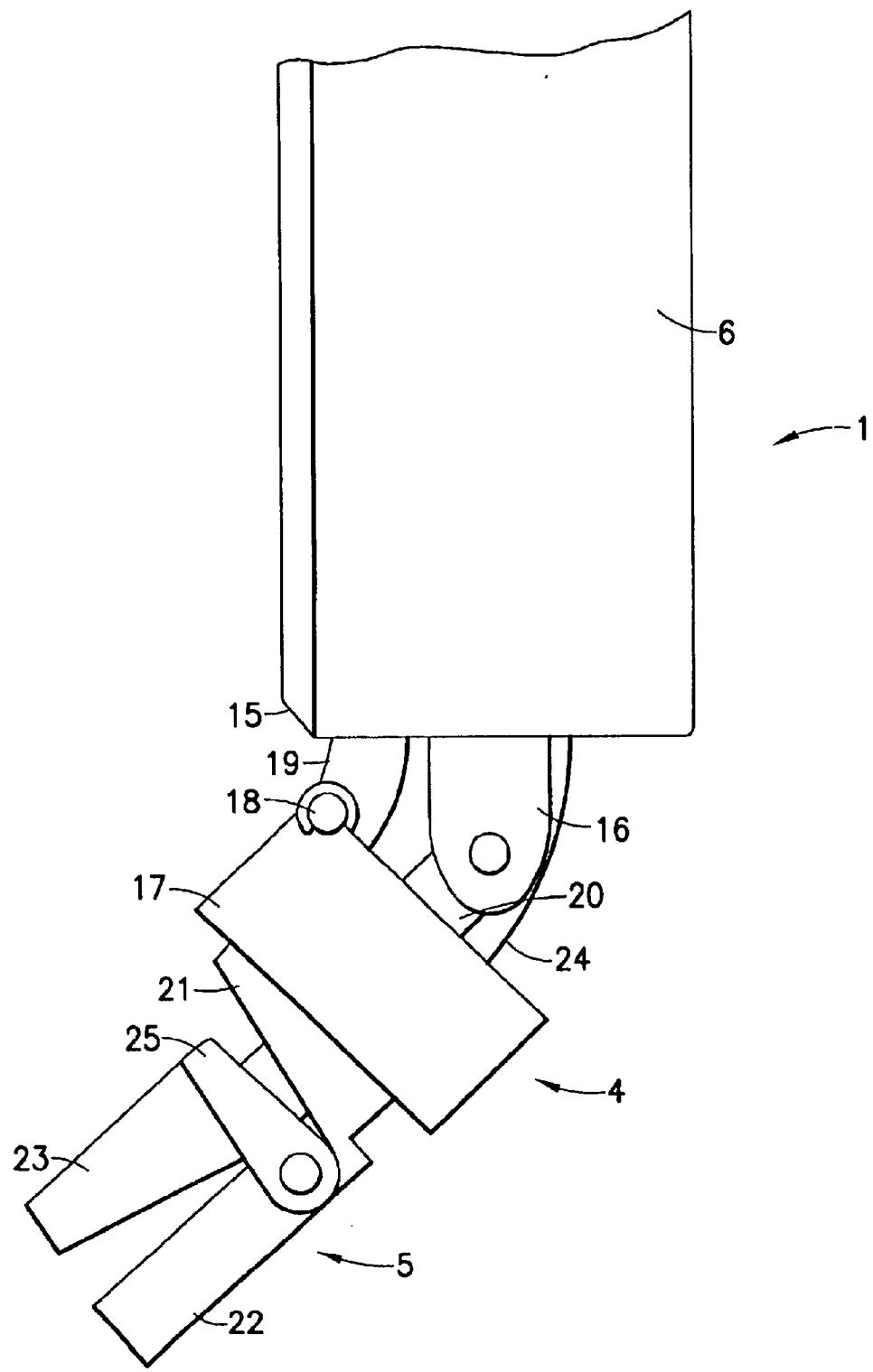
FIG. 5 is a side view of a bendable part of the surgical instrument of FIG. 1 including the mouth part supported therein.

The distal end portion of the tubular piece 6 has a chamfering 15 at a side associated with the bearing bore 14 (the left side according to FIG. 5). The chamfering 15 extends substantially straight at an angle of approximately 45° with respect to the front of the distal end of the tubular piece 6. In addition, two axially extending link lugs 16 are arranged at the distal end of the tubular piece 6 which are offset on both sides of the chamfering 15 by approximately 90° with respect to the length of the chamfering 15. The link lugs 16 include free ends with link bores or journals, the central axes of which are arranged in alignment with respect to each other.

The case-like seat 4 is formed by a cylindrical annular sleeve 17 or bearing bush preferably having outer and inner diameters corresponding to the tubular piece 6. One front edge of the cylindrical annular sleeve 17 facing the distal end of the tubular piece 6 includes a link point 18 such as, for example, a bearing eye or a joint cap for attaching and/or inserting a joint ball. The link point 18 is fixedly connected with the sleeve 17 and may be integrally connected therewith as one piece. A seat actuating rod 19 includes a counterpiece that is rotatably and/or movably linked to this link point 18. The counterpiece is shaped corresponding to the link point 18 as part of the actuating rod 19.

Link lugs 20 are arranged at the sleeve 17 on both sides of the link point 18 and are offset by approximately 90°. The link lugs 20 may be made as one piece with the sleeve 17 and have free ends with a through hole or a bearing journal located on a joint axis. These lugs 20 at the sleeve 17 are connected to the link lugs 16 at the tubular piece 6 through the journals and through holes such that the sleeve 17 is pivotable or bendable at the distal end portion of the tubular piece 6. The maximum pivoting angle is enlarged at least in one pivoting direction by the chamfering 15 at the distal end of the tubular piece 6 so that the sleeve 17 may be pivoted by about 180°, for example, from a position coaxial with respect to the tubular piece 6 to a pivoted position substantially in parallel beside the distal end of the tubular piece 6.

A piston-shaped rotary member 21 having an axial through-bore is supported in a rotatable manner inside the sleeve 17. However, the rotary member 21 is not displaceable in the sleeve 17. A beak-shaped projection 22 is connected at a distal axial end of the rotary member 21 opposed to the tubular piece 6. The beak-shaped projection 22 may be integrally connected to the rotary member 21 as one piece or by welding or soldering and extends in an axial direction. The projection 22 forms a first clamping jaw of the mouth part 5 which is not individually movable. A second clamping jaw 23 is linked hinge-like to the first clamping jaw or the rotary member 21 proximate the fastening area of the projection 22 and interacts with the projection 22 to form the mouth part 5 of the surgical instrument.

A flexible but torsion-resistant drive shaft 24 is fixed centrally at the end of the rotary member 21 facing the tubular piece 6, i.e. extending between the sleeve-side link lugs 20, a distal end of the drive shaft being rotatably supported in the tubular piece 6. The flexible drive shaft 24 extends along an axial through-hole provided in the tubular piece 6 substantially aligned with the through-bore in the rotary member 21. The rotary member 21 may optionally be formed integrally with the flexible drive shaft 24.

Inside the through-hole of the flexible shaft 24, an actuating cable 25 for the second hinge-like movable clamping jaw 23 is movably supported relative to the drive shaft 24 and is mounted on the second clamping jaw 23 for pivoting the same in response to tensile and/or pressure load.

Figure 4:
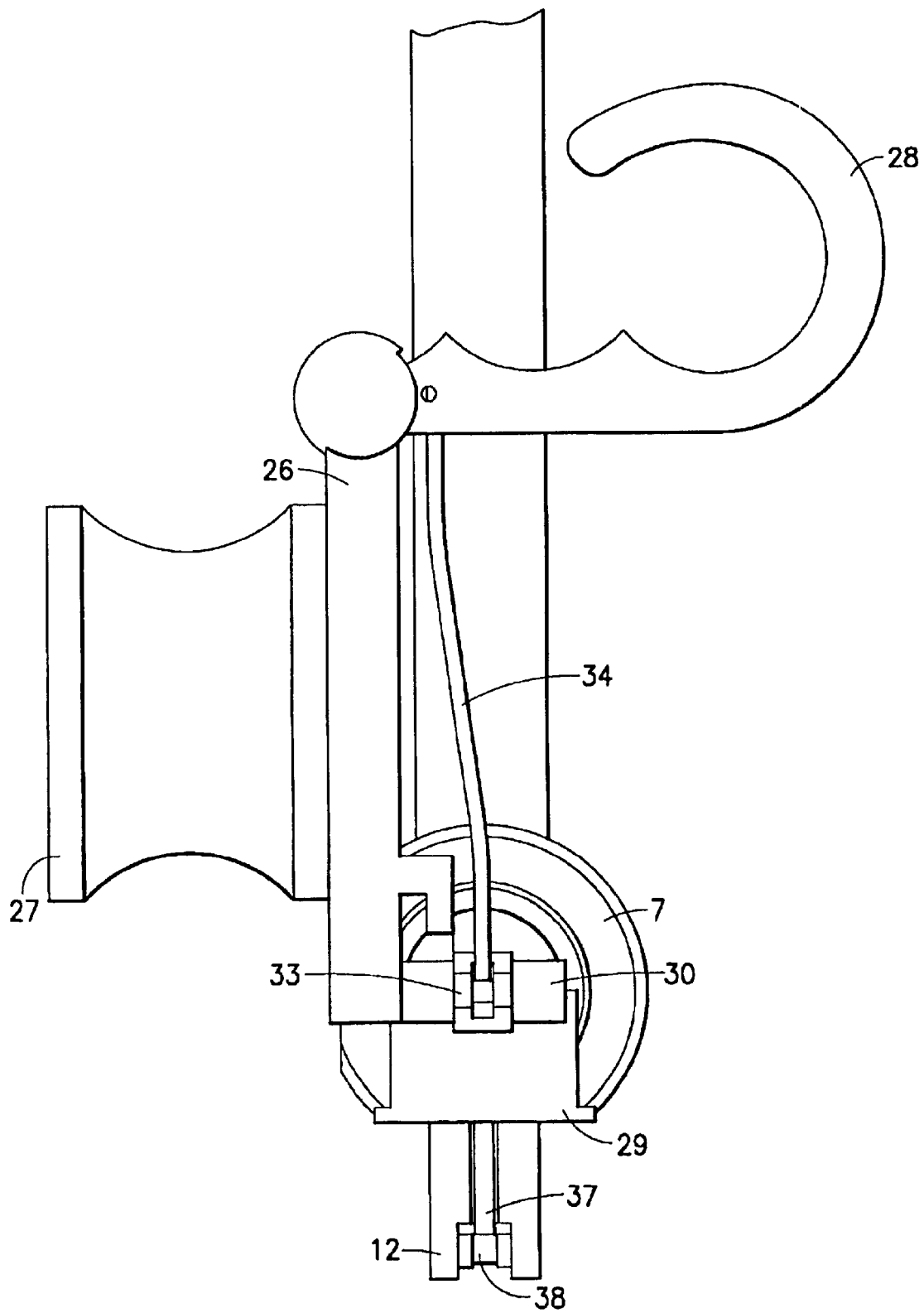
FIG. 4 is a top view of the actuating device of FIG. 2.

The actuating device 2 is mounted on and in the spherical cap 7 fixed to the proximal end of the hollow shank 1. According to FIGS. 3 and 4, the actuating device 2 has a handle in the form of a lever 26 to which a knob 27 or a differently shaped grip end is fixed. The knob is arranged so that it may be enclosed and held fast by an operator preferably by the thumb and the index finger of one hand. A catch 28 or trigger is arranged at the lever 26 and is movable relative to the lever 26. The catch is arranged in a position which is ergonomically suited concerning the knob 27 as a further part of the handle which is designed so that it is operable by at least one of the remaining fingers of the operator's hand.

A rear end of the lever 26 remote from the catch 28 is hinged on a bearing head 29 which is rotatably supported in the spherical cap 7. The bearing head 29 forms a link support 30 which is substantially U-shaped as shown in the view according to FIG. 4. A lateral swivel journal (not shown in detail) is disposed at a free end portion of the link support 30. The rear end of the lever 26 includes a transverse bore 31 in which the swivel journal is inserted. Between the legs of the U-shaped link support 30, a first toothed wheel or pinion 32 is rotatably held at a bolt or pin (not shown) which is formed at the link support 30 at a distance from the swivel journal. The first pinion 32 is designed in the form of a cam and eccentrically includes a link point (FIG. 3) approximately level with the swivel journal for connection to a pull-push bar 34. The pull-push bar 34 extends substantially along the lever 26 and is connected to the catch 28 at its other free end.

A second likewise preferably cam-shaped pinion 35 is in meshed engagement with the first pinion 32 and is movably held at the bearing head 29. Pinion 35 has an eccentric link point 36 to which an elongation rod 37 is mounted. The elongation rod 37 extends along the extension 11 of the spherical cap 7 to an outer link point 12 thereof. A rocker arm 38 to the outer end of which the elongation rod 37 is linked is centrally supported at this link point 12. Furthermore at the other outer end of the rocker arm 38 the proximal end of the actuating cable 25 is linked preferably via a spherical head for allowing a pivoting and torsion movement.

The catch 28, the pull-push bar 34, the two cam pinions 32, 35, the elonigation rod 37, the rocker arm 38, and the actuating cable 25 in this order form a mouth part actuation device as a gear train of the force and/or torque transmission mechanism.

The seat actuating rod 19 is connected to the lever 26 at a point on the lever between the support at the link support 30 and the catch 28. The seat actuating rod 19 also extends through the tubular piece 6 in parallel to the flexible torsion-resistant shaft 24 and exits the hollow shank 1 at the access 13 into the interior of the spherical cap 7. In this area the actuating rod 19 has at least a cardanic joint or a slide-resistant rod portion (not shown in detail) at which the actuating rod 19 is bent toward its connection point at the lever 26.

The flexible torsion-resistant shaft 24 is bent after exiting the tubular piece 6 inside the spherical cap 7 toward the longitudinal bore 10 of the extension 11 and is rotatably supported in the longitudinal bore 10. In the area of the portion of the shaft 24 which extends inside the spherical cap 7, the flexible shaft 24 has an external toothing 39. An internal toothing 40 formed at the bearing head 29 is in meshed engagement with the external toothing 39. To this end the bearing head 29 has a kind of sleeve 41 which is provided with the aforementioned internal toothing 40 and is movably supported in the spherical cap 7 while it encloses the flexible shaft 24. For a better guiding of the bearing head 29 it includes in addition a swivel journal 42 extending coaxially with respect to the sleeve 41 and/or the central axis thereof and being supported in the bearing bore 14 having a small diameter in the spherical cap 7 in the area between the inlet bore 8 and the access of the spherical cap 7.

The functioning of the surgical instrument according to the embodiment of FIGS. 1–5 is described as follows:

As already briefly indicated above, surgical instruments of this type require both the operation of the mouth piece, i.e., the opening and closing of the clamping jaws, and a horizontal pivoting and/or bending of the mouth part, i.e., the pivoting of the instrument tip by about at least 180° with respect to the tubular piece 6. Moreover the mouth part shall also be adapted to perform at least a 360° rotation about the longitudinal axis of the instrument tip.

The opening and closing of the mouth piece 5 is effected through the catch 28 as an individual actuating element which is actuated by one or more fingers of one hand of an operator. To this effect the operator grips the instrument according to the invention by the thumb and the index finger at the knob 27 and puts the other three fingers onto the catch 28. By pulling the catch 28 toward the knob 27, a force of pressure is applied to the push-pull bar 34 between the catch 28 and the first pinion 32, whereby the first pinion 32 is rotated. The second pinion 35 is rotated in response to the rotation of the first pinion. Hereby a force is applied to the elongation rod 37 eccentrically linked to the pinion 35 which swings the rocker arm 38 connected thereto. This horizontal-pivoting movement is converted into a translatory movement of the mouth part actuating cable 25 which is linked at the other end of the rocker arm 38 by the flexible shaft 24, corresponding, for instance, to a remote control for the trigger of a camera. By the translational movement of the actuating cable 25 the second clamping jaw 23 linked thereto is swiveled in the closing direction. By pressing the catch 28 in the opposite direction, the second clamping jaw 23 is swiveled in the opening direction.

Figure 2:
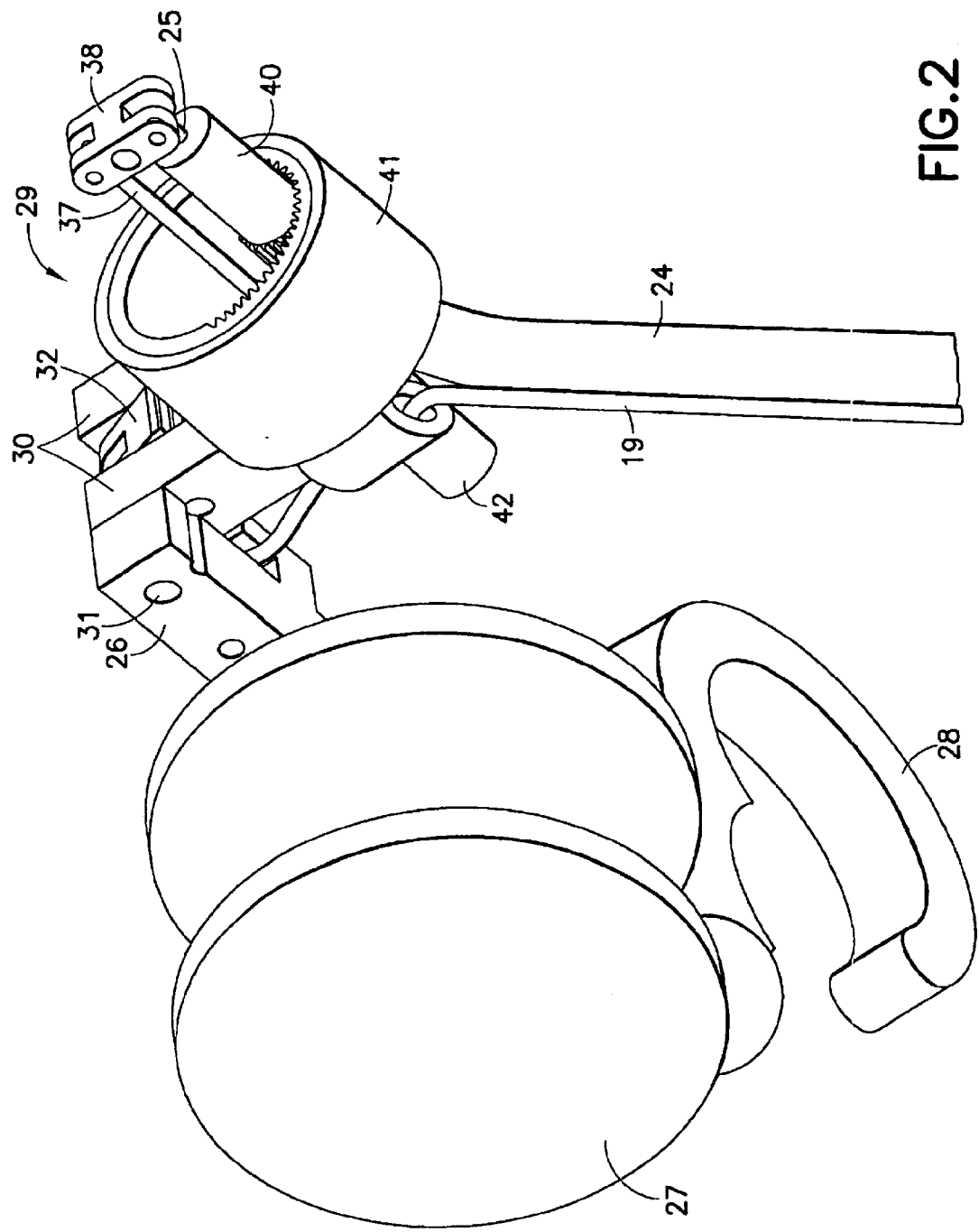
FIG. 2 is a cutaway perspective view of an actuating device of the surgical instrument of FIG. 1.

When the lever 28 is swiveled upwards about the rear link point 31 thereof corresponding, for instance, to an upwardly directed hand movement in the area of the wrist from the position shown in FIGS. 2 and 3, the seat actuating rod 19 fixed at the lever 26 between the link point 31 and the knob 27 is pulled out of the access opening 13 of the spherical cap 7. The pulling of the actuating rod transmits a tensile force to the sleeve 17 linked at the distal end of the tubular piece 6 by the link point 18 of the seat actuating rod 19. Accordingly the sleeve 17 is pivoted about the swivel journals at the link lugs 16 and thus follows the swiveling movement of the operator's hand. As the sleeve 17 pivots, the shaft 24 is correspondingly bent in the section between the distal end of the tubular piece 6 and the sleeve 17.

When the operator's hand is turned about the longitudinal axis of the forearm, the bearing head 29 is swiveled about the swivel journal 42 and the sleeve 41 inside the spherical cap 7. The flexible shaft 24 is rotated via the internal and external toothing 39, 40 at a predetermined transmission ratio about its longitudinal axis in response to the swivel movement. Accordingly, the shaft 24 rotates inside the longitudinal bore 10 of the extension 11 and inside the tubular piece 6, wherein the angular position of the extension 11 relative to the tubular piece 6 entails a continuous bending of the shaft 24 inside the spherical cap 7. By the rotation of the flexible shaft 24 the rotary member 21 and thus the mouth part 5 mounted thereto is rotated inside the seat 4, while the seat 4 itself is held fast by the hinge-like link connection to the tubular piece 6.

When the shaft 24 is rotated in the tubular piece 6, the mouth part actuating cable 25 is likewise rotated due to friction. The spherical head linking of the actuating cable 25 to the rocker arm 38 permits such a rotation, without exposing the actuating cable 25 to torsional forces. When pivoting the lever 26 about its rear link point 31, the position of the catch 28 also changes with respect to the first pinion 32. Since the linking of the connecting rod 37 between the pinion 32 and the catch 28 is substantially level with the link point 31 of the lever 26, the first pinion 32 remains substantially unactuated when the lever 26 is pivoted about the rear link point. The universal joint and/or the flexible section of the actuating rod 19 for swiveling the seat 4 is approximately located on the swivel axis of the bearing head 29 inside the spherical cap 7. Thus the longitudinal position of the seat actuating rod 19 also remains uninfluenced by a swivel movement of the bearing head 29.

The transmission ratio for actuating the mouth part 5, i.e., the second clamping jaw 23, may be adjusted at the pinions 32, 35, the link point of the connecting rod 34 at the catch 28 and/or the lever ratio at the rocker arm 38. The transmission ratio for actuating the seat 4 may be adjusted most suitably by choosing the connection point of the seat actuating rod 19 at the lever 26. The transmission ratio for rotating the mouth part 5 is finally determined by the selection of the internal and external toothings 39, 40 at the sleeve 41 of the bearing head 29 and/or at the flexible shaft 24. Preferably a mouth part rotation of up to 300° is achieved in a movement of rotation of the lever 26 and thus of the bearing head 29 of 90°. Furthermore, the axis of rotation for the rotation of the wrist to effect the rotation of the mouth part is inclined according to the arrangement of the inlet and outlet bores 8, 9, i.e., the hollow shank axis, by approximately 45°.

A second embodiment of the present invention will now be described with reference to FIGS. 6–11, wherein the same reference numerals are used for similar parts in the above-described embodiment.

Figure 6:
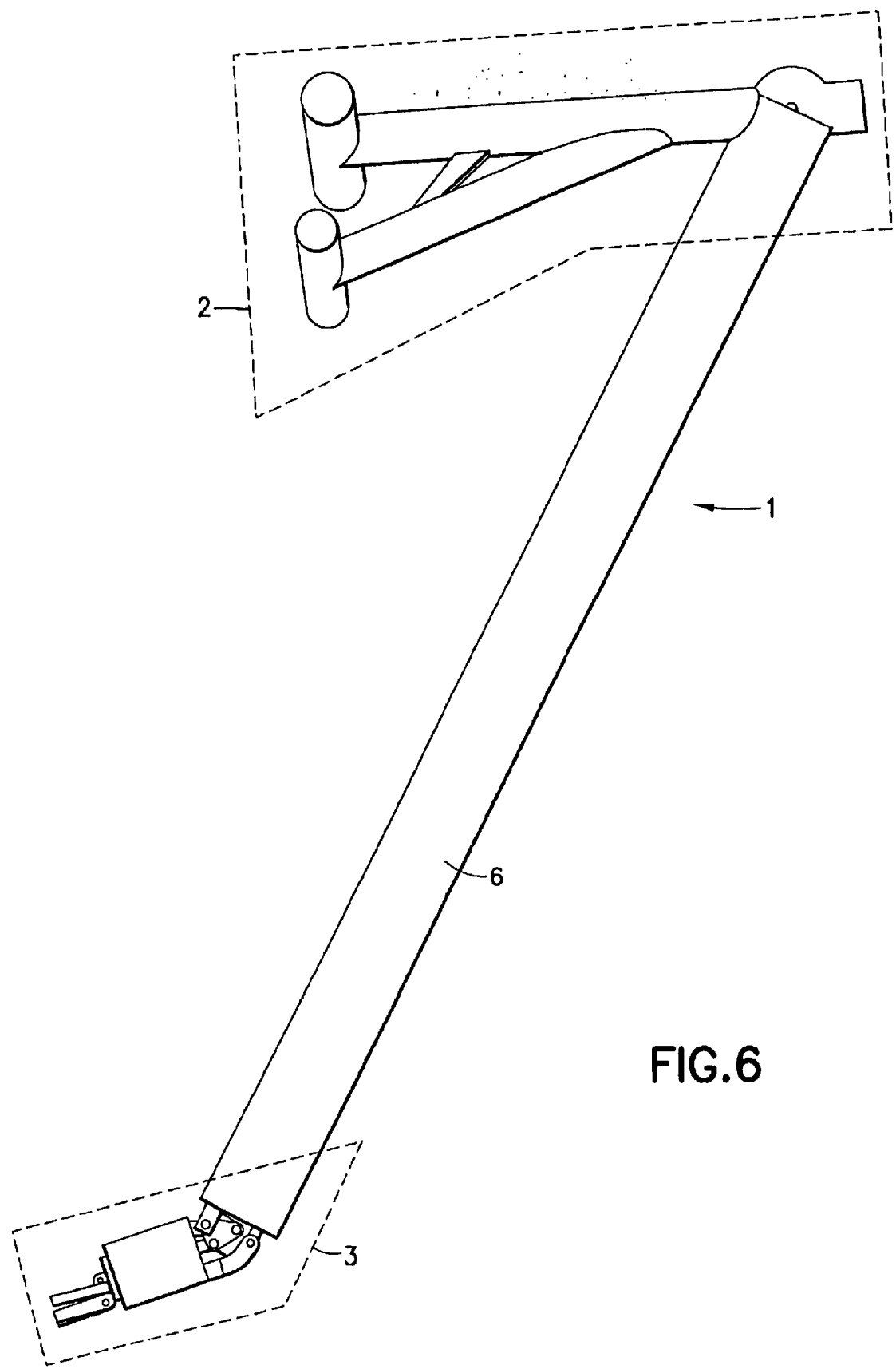
FIG. 6 is a side view of a surgical instrument for minimally invasive surgery according to another embodiment of the present invention.

In accordance with FIG. 6, a further embodiment of the surgical instrument likewise comprises an actuating device 2 or a grip end, a hollow shank 1 and an instrument tip 3 which is mechanically coupled with the grip end by a force/torque transmission mechanism.

The hollow shank 1 includes a substantially inflexible tubular piece 6 made of a non-oxidizing material which is cut square at its two ends. A bracket-shaped projection 50 is formed or fastened to the distal end of the hollow shank 1 (see FIG. 7). A through hole aligned tangentially with respect to the tubular piece 6 is arranged at an edge side of the projection 50. A mounting structure for attaching the actuating device is formed at the proximal end of the hollow shank 1.

Figure 7:
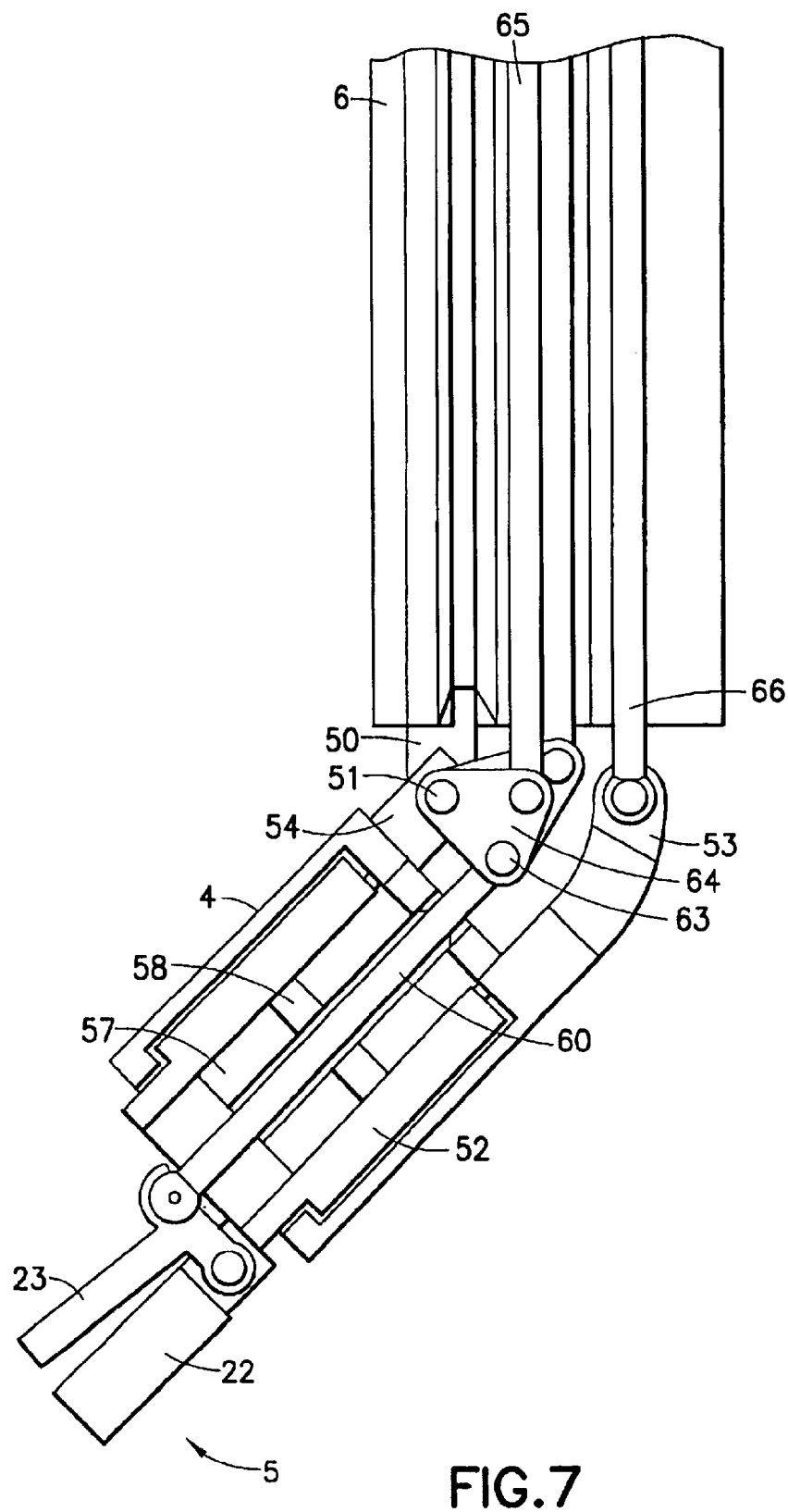
FIG. 7 shows the side sectional view of a bendable part including a rotatably supported mouth part according to the embodiment of FIG. 6.
Figure 8:
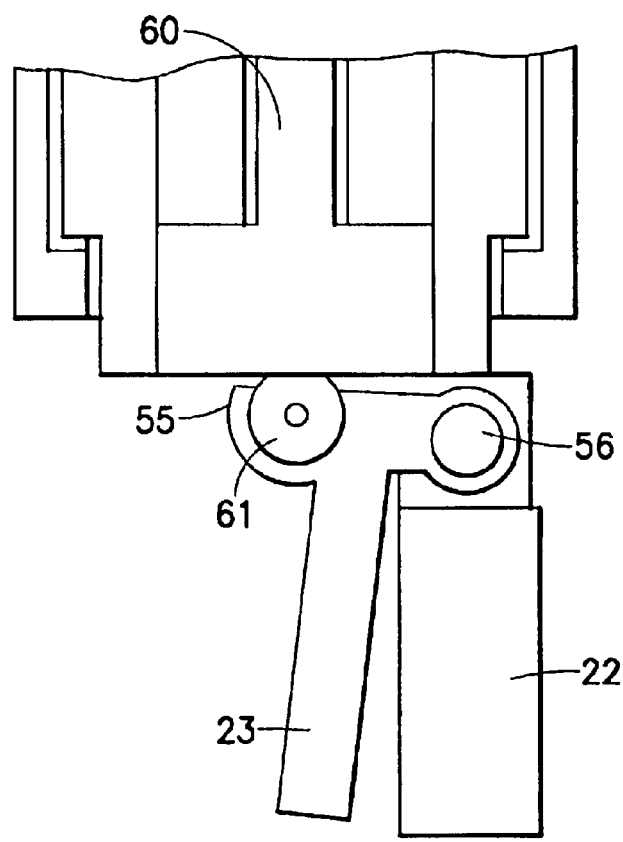
FIG. 8 is a detailed side view of the mouth part shown in FIG. 7.

According to FIGS. 7 and 8, the instrument tip 3 has a case-like substantially cylindrical seat 4. A cylindrical rotational body 52 is rotatably supported but axially fixed in the cylindrical seat 4. A side of the seat 4 facing the tubular piece 6 includes an axially extending strap 53 arranged eccentrically and preferably at an edge side thereof. A strap link point is formed at the free end of the strap 53 as a through hole or a spherical head cup. At an edge side of the seat 4 opposing the strap 53 an axial bracket 54 is formed, a free end of which likewise includes a through bore. The axial bracket 54 is movably hinged to the axial projection 50 of the tubular piece 6 by a pin 51.

Figure 8A:
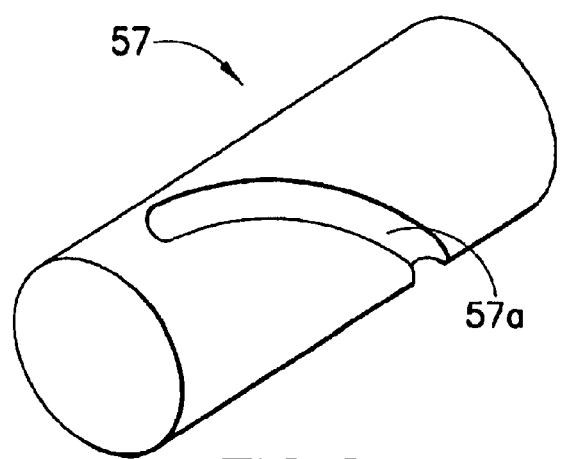
FIG. 8a is a perspective view of a piston of the bendable part shown in FIG. 7.

An axially extending projection 22 which forms a first clamping jaw of a mouth piece 5 is formed preferably in one piece with the rotational body at a distal end of the rotational body 52. A second clamping, jaw 23, which has a link point 55 in the form of a spherical head cup at a jaw portion located approximately in the central axis of the rotational body 52, is hinged to the projection 22 at a point 56. Inside the rotational body 52, an axially movable piston 57 is supported that fixed with respect to rotation rotation. The piston 57 has a spiral groove 57a (shown in FIG. 8a) on its outer surface. The rotational body 52 includes at least one radially inwardly protruding follower pin 58 which slidingly engages in the spiral groove such that in the case of an axial movement of the piston 57 the rotational body 52 is rotated about its longitudinal axis by the interaction of the spiral groove and the follower pin 58.

The piston 57 includes a central through-bore 59 which extends axially and is arranged approximately in alignment with respect to the link point 55 of the second movable clamping jaw 23 of the mouth part 5. A pull-push bar 60 is axially movably supported inside this through-bore 59. A spherical head 61 is formed at distal end of the pull-push bar 60 which is received in the link point 55 of the second clamping jaw 23. A section of the pull-push bar 60 includes a joint or a flexible intermediary 62. Furthermore, the proximal end of the pull-push bar 60 is provided with a spherical head or a bearing eye 63.

The force/torque transmission mechanism in FIG. 7 comprises a central baffle plate 64 in the area of the instrument tip 3 which is movably linked to the link point of the bracket 54 and/or the hinge pin 51 that is put through the through hole of the bracket 54. The baffle plate 64 is also linked to the projection 50 disposed at the side of the tubular piece 6 by this connection. The central baffle plate 64 has a triangular shape in the present case and includes two further serial through holes (disposed in the edge portions of the plate). The pull-push bar 60 is hingedly connected to one of these through holes while a mouth part actuating rod 65 guided in the tubular piece 6 is hingedly connected to the other through hole.

Moreover the force/torque transmission mechanism includes a seat actuating rod 66 which is likewise guided in the tubular piece 6 and is hinged to the strap link point of the strap 53.

Figure 9:
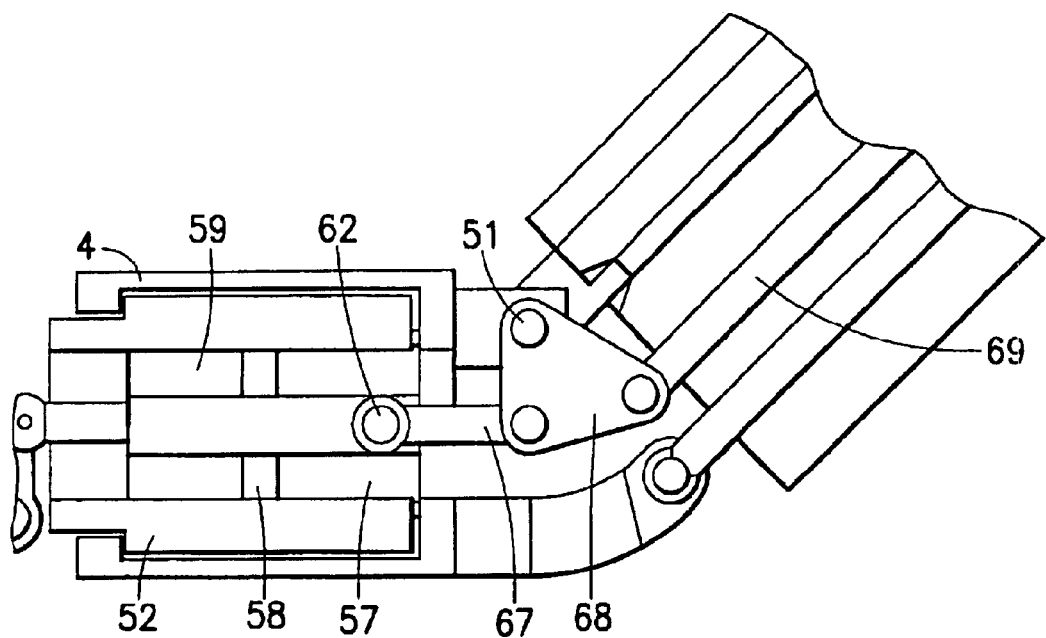
FIG. 9 is a sectional view of the bendable part of FIG. 7.
Figure 10:
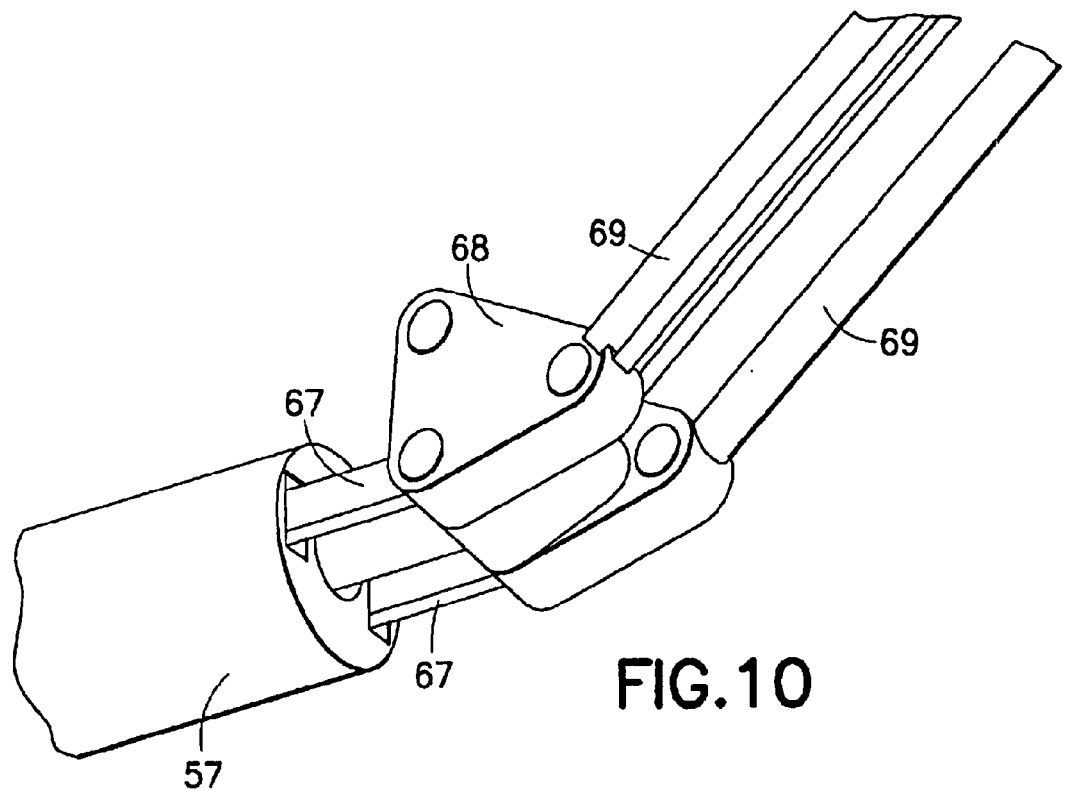
FIG. 10 is a detailed view of deflection rods for the rotation and the actuation of the mouth part in their position relative to each other for the bendable part of FIG. 7.

Referring now to FIGS. 9 and 10, two axial bolts 67 are fixed to the piston 57 on both sides of the compression/tension bar 60. Each of the axial bolts 67 has a bearing eye at their ends protruding from the piston 57. At the hinge pin 51 for movably supporting the seat 4 on the tubular piece 6, two lateral baffle plates 68 are movably arranged on both sides of the central baffle plate 64. The two bolts 67 are respectively linked to the two lateral baffle plates 68, which each have a design identical with the central baffle plate 64. Furthermore, piston actuating rods 69 movably guided in the tubular piece 6 are respectively hingedly connected to the lateral baffle plates 68.

Figure 11:
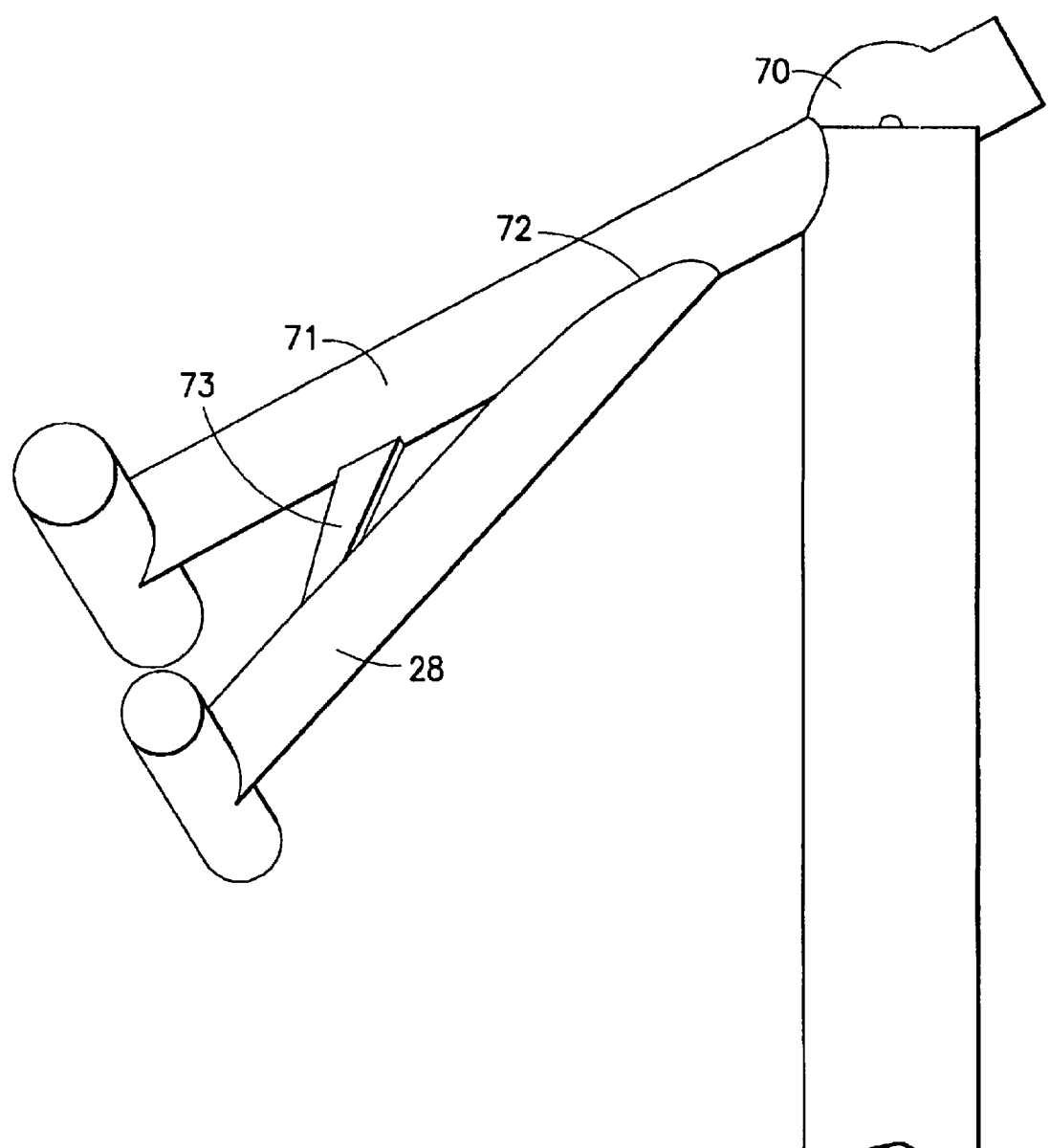
FIG. 11 is a side view of the operating elements of an actuating device according to the surgical instrument of FIG. 6.

All of the actuating rods 65, 66, and 69 are linked to the actuating device 2. According to FIG. 11, the actuating device 2 includes a joint mechanism 70 which is shown in FIG. 11 as a spherical joint. A grip end 71 is linked to the proximal end of the tubular piece 6 by the joint mechanism such that the tip end 71 is adapted to be hinge-like swiveled with respect to the tubular piece 6 and is additionally adapted to be twisted and/or rotated about its longitudinal axis. In addition, a catch 28 is slidably hinged at the grip end 71 at a point 72.

The two piston actuating rods 69 are linked to the grip end 71 such that a twisting movement of the grip end 71, i.e., a rotation of the grip end about its longitudinal axis, is converted into a shifting movement of the piston actuating rods 69. The seat actuating rod 66 is also linked to the grip end 71 such that a swiveling movement of the grip end 71 with respect to the tubular piece 6 results in a shifting movement of the seat actuating rod 66, while the piston actuating rods 69 remain immobile. The mouth part actuating rod 65 is deflected in the joint mechanism area 70 to a shear transmission element 73 hinged to the catch 28. An actuation of the catch 28 results in a displacement of the mouth part actuating rod 65 inside the tubular piece 6.

The function of the instrument according to the embodiment of FIGS. 6–11 is described as follows:

As shown in FIG. 11, the grip end 71 has a rod member with a cross bracket as a handle at its outer end. The cross bracket is gripped by the operator's hand such that the rod member extends along the forearm of the operator toward the operator's elbow. The catch 28 is linked to the rod member so that it can be reached and actuated by the fingers of the operator's hand which is holding the grip end 71. The length of the rod member, i.e. the distance between the joint mechanism 70 and the cross bracket, is dimensioned so that the joint mechanism 70 is arranged substantially below the operator's wrist.

When the catch 28 is actuated, the shear transmission element 73 is longitudinally displaced. This movement is transmitted to the mouth part actuating rod 65 inside the tubular piece 6 which is linked to the central deflection plate 64 and swivels the same about the hinge pin 51. The swivel movement of the central deflection plate 64 is transformed into a shifting movement of the pull-push bar 60 inside the piston 57. The deformable section and/or the joint 62 compensates for height variations of the proximal end of the pull-push bar 60 due to the swivel movement of the central baffle plate 64. The displacement of the pull-push bar 60 causes a swivelling of the second clamping jaw 23 in the opening or closing direction.

For bending the seat 4, the entire grip end 71, i.e., the rod member in the joint mechanism 70, is swiveled or pivoted with respect to the tubular piece 6. This movement displaces the seat actuating rod 66 inside the tubular piece 6 and applies force to the bend strap 53. In response, the seat 4 bends or pivots about the hinge pin 51. In the preferred embodiment, a first extreme position is reached in which the instrument tip 3 is arranged substantially in alignment with the tubular piece 6. Depending on the structural shape, a second extreme position may be bent about 180° and thus point upwards at the outside located in parallel to the tubular piece 6. Accordingly, the bending of the seat 4 in combination with a rotation of the tubular piece 6 itself allows each point on the inner surface of an imaginary ball having the radius which is predetermined by the length of the bendable instrument tip 3 to be reached.

For rotating the mouth part 5, the rod member of the grip end 71 is twisted and/or rotated about the central axis thereof. This rotating movement is transformed into a shifting movement of the piston actuating rods 69 at the joint mechanism 70 which exclusively admits the bending and the rotation of the rod member. This displacement of the piston actuating rods 69 along the tubular piece 6 is deflected by the lateral baffle plates 68 into a shifting movement of the piston 57 which slides axially inside the rotational body 52. The catch pins 58 of the rotational body 52 engaging in the spiral groove provided on the piston 57 transform the sliding movement of the piston 57 into rotation of the rotational body 52 corresponding to the gradient of the spiral groove as a transmission mechanism. The mouth part 5 fixed to the rotational body 52 is rotated therewith. During this rotation of the mouth part 5, the pull-push bar 60 simultaneously rotates at its distal spherical head 61 in the link point 55 of the mouth part 5 so that the actuating function thereof remains uninfluenced by the rotation of the mouth part 5.

Accordingly, three distinct functions are realized in the instrument tip 3 as follows: (1) the seat 4 may be bent with respect to the tubular piece 6, (2) the rotational body 52 which is bent together with the seat 4 may be rotated in any bending position, and (3) the mouth part 5 may be actuated in any bending and rotational position. As in the previous embodiment, the mouth part 5 may be designed as a needle holder, fixation forceps, or scissors. Due to the aforementioned function of the joint mechanism, a lateral swiveling of the rod member produces a rotation of the tubular piece 6 as a whole so that the instrument tip 3 may be horizontally and vertically displaced by the actuating device 2 and may be rotated together with the tubular piece 6 and bent with respect to the tubular piece 6. In addition, a rotation of the mouth part 5 is possible inside the instrument tip 3 and an actuation of the mouth part 5 is possible via the actuating device 2.

The following describes alternative gear and/or force and torque transmission mechanisms which may be used with the present invention. Each alternative embodiment has in common the immediacy when transmitting an actuating movement of the actuating device to the instrument tip and preferably at a predetermined transmission ratio.

Figure 12:
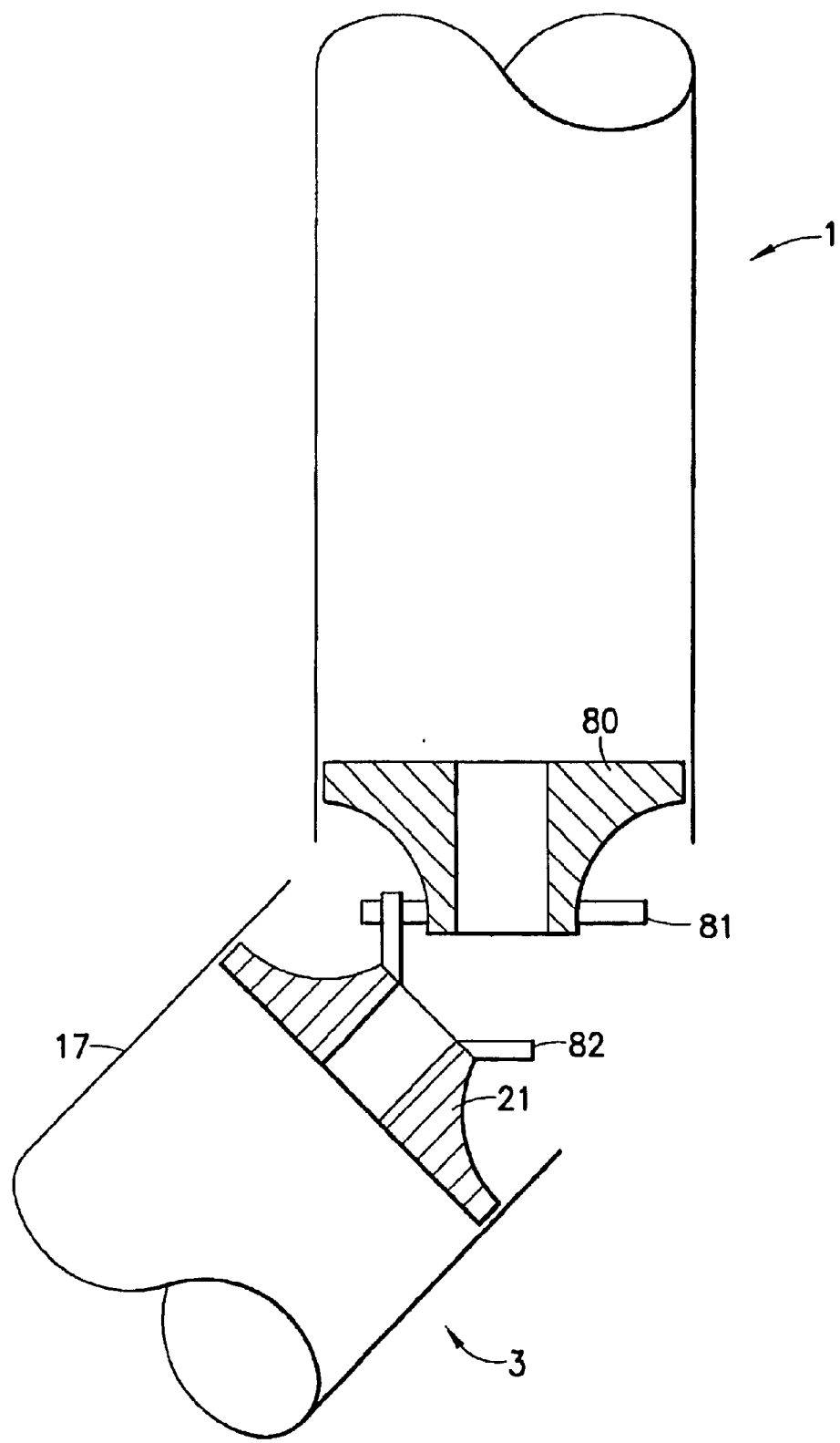
FIG. 12 is a schematic side view of a connecting portion of an instrument tip to a hollow shank according to a further embodiment of the present invention.

FIG. 12 illustrates an embodiment of the present invention in the hinge area between the instrument tip 3 and the hollow shank 1. All other technical configurations of this embodiment, especially of the actuating device and the support of the mouth part may correspond to the previously described embodiments and therefore are not explained in detail in this context.

In accordance with FIG. 12, the torsion-resistant flexible shaft used in the first embodiment is replaced at least partly with a rigid rotary shaft 80. At least the connecting portion of the flexible shaft where the instrument tip 3 and the hollow shank 1 meet (shown in FIG. 12) is axially connected to the rigid shaft 80. As shown in FIG. 12, the distal end of the rigid rotary shaft 80 at the distal end of the hollow shank includes an external toothing such as, for example, a spherically arched conical gearwheel or a number of radial pins 81. The rotary member 21 likewise known from the previous embodiments also includes an external toothing at its end portion facing the hollow shank 1 such as, for example, pins 82 projecting radially outwardly about 45° with respect to the longitudinal axis thereof. The pins 81, 82 are in meshed engagement so that a torque from the rigid shaft 80 may be transmitted to the rotary member 21. The instrument tip 3 itself is linked to the hollow shank 1 as in the previous embodiments and the actuating cable for the mouth part (both are not shown in FIG. 12) is correspondingly laid inside the rigid shaft 80 and inside the rotary member 21.

The operation of the instrument according to the embodiment of FIG. 12 corresponds to that of the previous embodiments except for the fact that when the instrument tip 3 is bent with respect to the hollow shank 1 the radial pins 81 vary their respective angles of mesh with respect to the opposite pins 82 of the rotary member 21.

Accordingly, the torsion-resistant flexible shaft of the previous embodiments may be completely dispensed with in the area of the actuating device. More specifically, if the gear including pins 81 and 82 is arranged in the hinge area between the instrument tip 3 and the hollow shank 1, the flexibility of the shaft is not required in this position. Since the shaft according to the first embodiment of FIGS. 1–5 is likewise bent in the area of the actuating device, the first embodiment exploits the flexibility of the shaft. The embodiment of FIG. 12 provides a joint in the position of the bend for connecting two individual parts of a now completely rigid shaft with each other.

Figure 13:
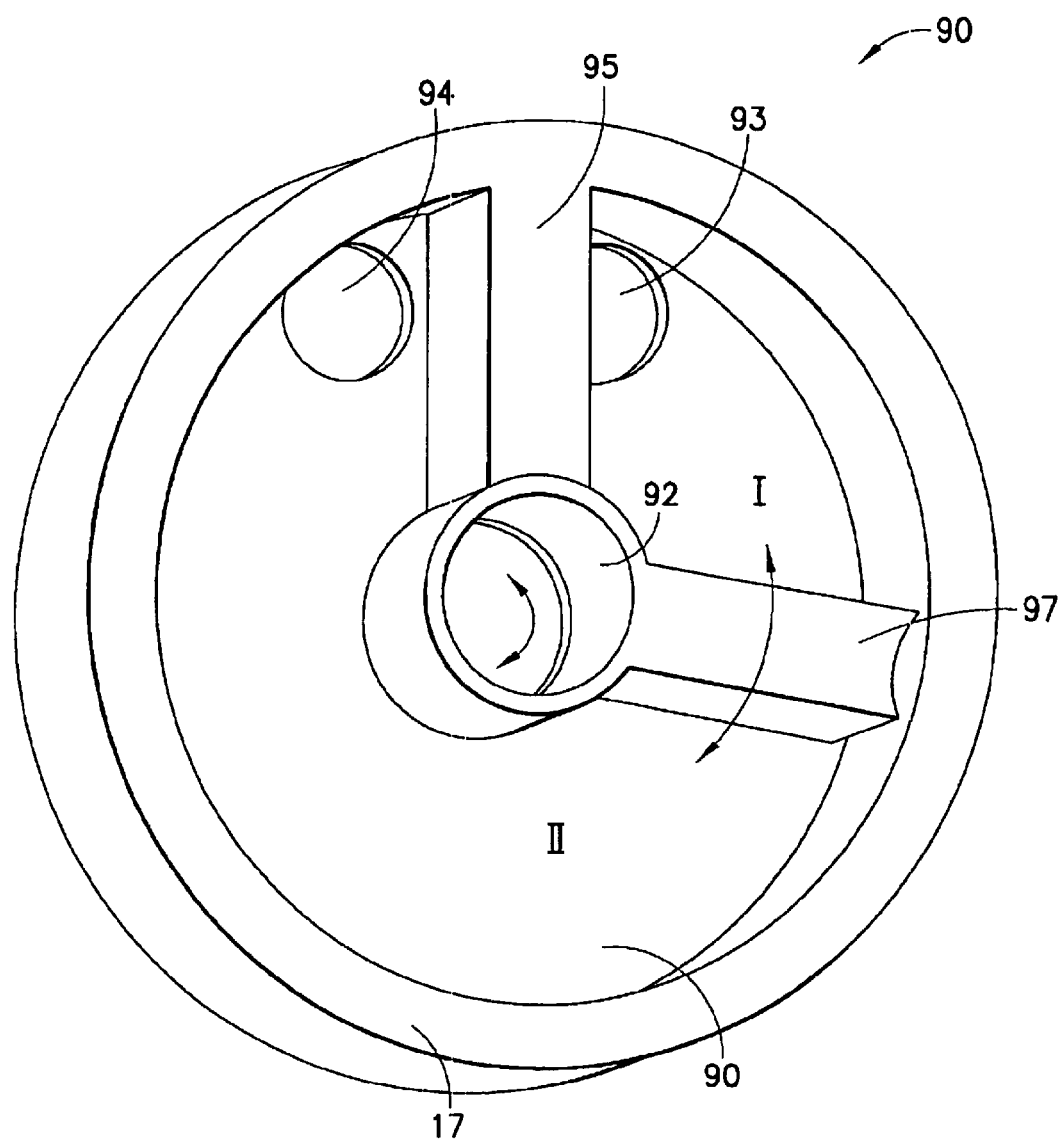
FIG. 13 is a perspective cross-sectional view of an instrument tip having a hydraulic or pneumatic drive and/or gear according to another embodiment of the present invention.

The embodiment according to FIG. 13 includes a hydraulically or pneumatically operative device 90 interposed between the rotary member and the actuating device (both are not shown in FIG. 13) in the gear mechanism.

Figure 13A:
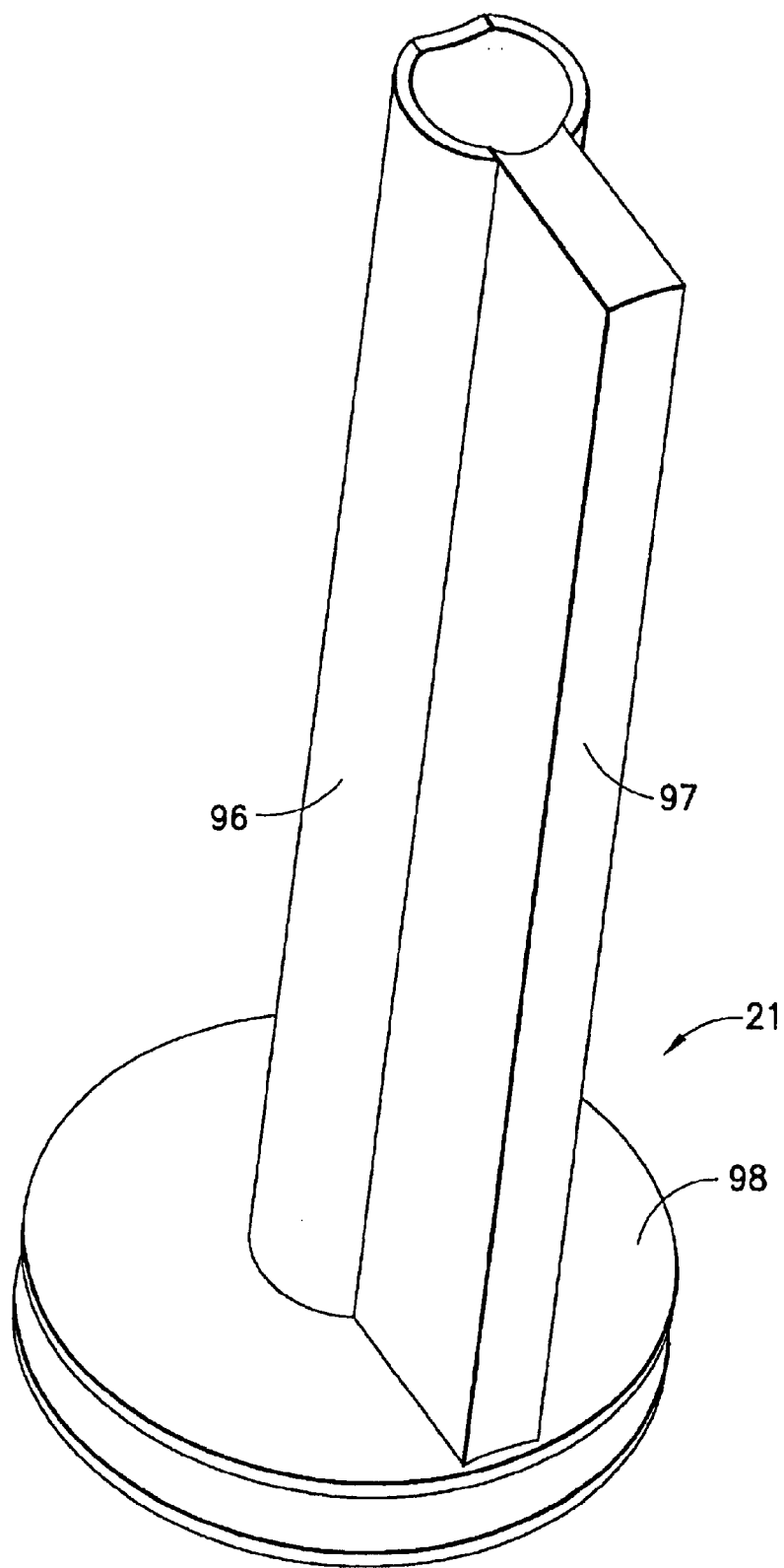
FIG. 13a is a perspective of a rotary piston for use with the instrument tip of FIG. 13.

In principle, a manual actuating movement of the actuating device is transmitted to the instrument tip such that the mouth part performs a rotation inside the instrument tip. As described in the above embodiments, the transmission of the manual actuating movement may be effected by a purely mechanical gear mechanism or a combined mechanically hydraulic/pneumatic gear mechanism. In the embodiment according to FIGS. 13 and 13*a*, the rotary member known from the first embodiment is designed as a rotary piston 21 which is rotatably supported in the instrument tip, i.e., in the sleeve 17. As in the first embodiment, the sleeve 17 itself is bendably or pivotably supported on the hollow shank and is swiveled or pivoted as described above.

According to FIG. 13, at least the end face of the sleeve 17 facing the hollow shank 1 is closed by a front wall 91 into which three through-bores 92, 93, 94, i.e., a central bore 92 as well as two decentrally arranged pressure connection bores 93, 94, are introduced. The two decentralized bores 93, 94 are separated by a longitudinally extending partition web 95 extending toward the central bore 92 which includes a sealing strip (not shown) at its radially inward edge. The rotary piston 21 includes a small tube 96 (see FIG. 13*a*) which is sealingly supported in the central bore 92 and is guided fluid-tight at the radially inner edge of the web 95. A circular plate 98 is fixed at the distal end of the small tube 96 for sealingly closing the distal end of the sleeve 17. The rotary piston 21 is held in the sleeve 17 so that it is rotatable relative to the sleeve but substantially fixed with respect to axial displacement in the sleeve 17.

As further shown in FIG. 13, the small tube 96 has an axially extending and radially projecting strip 97. A radially outer edge of the radially projecting strip 97 grazes sealingly at the inside of the sleeve 17. The web 95, the small tube 96 and the strip 97 define two fluid-tight separated pressure chambers I, II are formed each of which includes one of the pressure connections 93, 94 and the volumes of which vary in dependence on each other according to the angular position of the strip 97 with respect to the web 95.

When a fluid is pressed into the pressure chamber I and when a corresponding amount of fluid flows out of the pressure chamber II, the rotary piston 21 rotates according to the changes of volume of the two pressure chambers I, II in the direction of the arrow shown in the center of FIG. 13.

The pressure buildup or reduction in the pressure chambers I, II represented in FIG. 13 is preferably effected via a manual pump not shown in detail. The manual pump may, for example, be accommodated in the hollow shank 1 or directly in the area of the actuating device and is operated by the actuating device such as the actuating device in the embodiment of FIGS. 6–11. That is, the rods 69 shown in FIG. 10 may be used. However, instead of being connected to a piston inside the instrument tip, the rods may be connected to a piston of the manual pump having pump chambers connected to the pressure chambers I, II through hoses inside the hollow shank 1. The gear and/or the transmission ratio for transforming an actuating movement of the actuating device into a rotation of the rotary piston is determined on the basis of the volume ratio of the pressure chambers I, II to the pump chambers.

Figure 14:
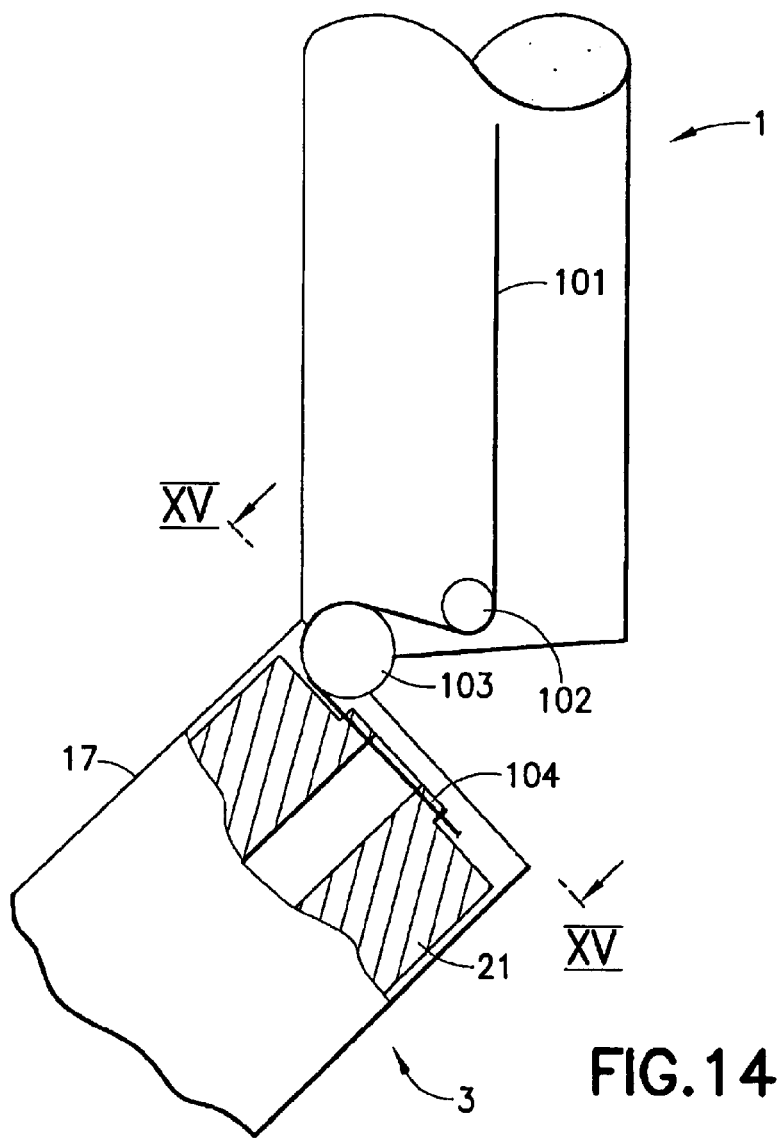
FIG. 14 is a schematic side view of a connecting portion of an instrument tip to a hollow shank according to another embodiment of the present invention.
Figure 15:
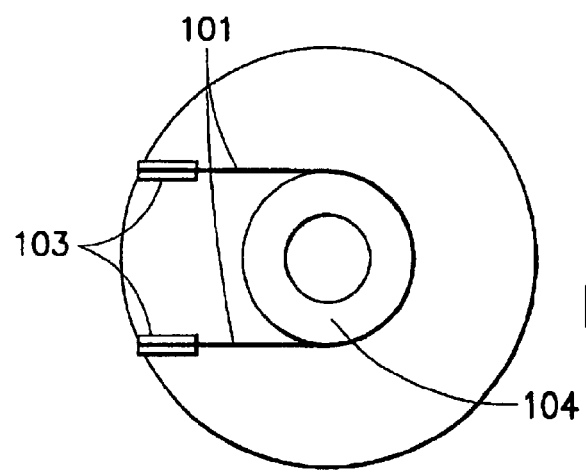
FIG. 15 is a top view of the connecting portion as viewed along line XV—XV in FIG. 14.

FIGS. 14 and 15 show a further embodiment of the present invention in the hinge area between the instrument tip 3 and the hollow shank 1. The actuating device according to this embodiment may, for example, comprise the embodiment of the actuating device used in FIGS. 6–11.

In contrast to the embodiment of FIGS. 6–11, the embodiment of FIGS. 14 and 15 includes two Bowden cables 101 instead of the rods 69. The Bowden cables 101 are linked on both sides of the handle (not shown in FIG. 14) of the actuating device and preferably turn a manual rotation about the forearm into a movement of translation opposed to each other. At the distal end portion of the hollow shank 1 there are arranged two rollers 102 aligned coaxially with respect to each other whose rotating direction follows the longitudinal axis of the hollow shank. The common axis of the rollers 102 is normal to the longitudinal axis of the hollow shank 1. Radially offset with respect to the axis of the hollow shank, two further deflection rollers 103 having rotating directions equal to the rollers 102 are supported in the hollow shank 1, wherein the deflection rollers 103 are preferably located on the hinge axis of the instrument tip 3 and of the hollow shank 1.

The rotary piston 21 supported in the instrument tip 3 and/or in the sleeve 17 likewise includes, according to FIG. 14, a running wheel 104 which is centrically fastened in front of the proximal end of the piston 21. The two Bowden cables 101 are guided around the rollers 102, the two deflection rollers 103 as well as the running wheel 104 in this order and are interconnected at their ends to form single cords. By this guiding of the cords an opposed movement of translation of the Bowden cables 101 inside the hollow shank 1 is converted into a rotation of the rotary piston and/or rotary member 21, wherein the transmission ratio between the actuating movement of the actuating device and the rotation of the rotary piston 21 and thus of the mouth part (not shown) is substantially defined by the diameter of the running wheel 104.

FIGS. 16 and 17 show a further embodiment for a torque and force transmission mechanism in accordance with the present invention in the connecting area between the tubular piece and/or the hollow shank 1 and the instrument tip 3.

According to this embodiment, drive ropes, elastic strands or chains 110, 111 are guided in the hollow shank 1 which are linked at their proximal ends to an actuating device not shown in detail. It is emphasized in this context that concerning the design of an actuating device, two different embodiments have been shown and described above. However, any actuating device may be used that is adapted to the torque and force transmission mechanism as long as the ergonomics of a human hand are taken into account.

In accordance with FIGS. 16 and 17, the drive ropes or strands 110, 111 drive two opposed coaxial wheels 112, 113 (frictional wheels or chain wheels) each of which is respectively connected to a conical gearwheel 114, 115 so as to be secured against rotation. The common axial center line of the two separate wheels 112, 113, including the conical gearwheels 114, 115, is normal to and intersects the center line, i.e., longitudinal axis, of the tubular piece 6 or hollow shank 1. The axles of the two pairs of wheels 112, 113 are mounted at the distal end of the hollow shank 1 and may also comprise the linking and swivel axles for the instrument tip 3. In the section of the instrument tip 3 facing the hollow shank 1, i.e. in the seat (not shown in detail), a further conical gearwheel 116 is supported such that the center line thereof extends coaxially with respect to the center line of the seat. This further conical gearwheel 116 is fixedly connected to the mouth part (not shown in FIGS. 16 and 17) and/or the rotary member 21 and is in meshed engagement with the two conical gearwheels 114, 115 supported in the hollow shank 1. The further conical gearwheel 116 preferably has a larger diameter than the two conical gearwheels 114, 115 in the hollow shank 1, the frictional or chain wheels 112, 113 in turn having a smaller diameter than the pertinent conical gearwheels 114, 115.

The operation of the torque and force transmission mechanism in accordance with FIGS. 16 and 17 is as follows:

When both frictional wheels 112, 113 are driven in the same direction of rotation at the same rotating speed by the strands or chains 110, 111, a swivel moment is transmitted to the instrument tip 3 via the large-diameter conical gearwheel 116 such that the instrument tip 3 bends with respect to the hollow shank 1 while the axes of wheels 112, 113 form the swivel point. If the conical gearwheel 116 is dimensioned to have a large diameter than the conical gearwheels 112, 113, the conical gearwheels remain in meshed engagement even at a pivoting angle of about 180° so as to be adapted to transmit the swivel moment. The two small-diameter conical gearwheels 112, 113 may be supported elastically on the axles thereof to guarantee the meshed engagement with the conical gearwheel 116.

If the mouth part is to be rotated in the seat at a present bending position of the seat, the two frictional wheels 112, 113 are driven on the basis of their present position of rotation (relative zero position) now in opposite directions at the same amount of rotating speed to rotate the large-diameter conical gearwheel 116 about its central axis, thereby rotating the mouth part.

Thus, while there have shown and described and pointed out fundamental novel features of the invention as applied to a preferred embodiment thereof, it will be understood that various omissions and substitutions and changes in the form and details of the devices illustrated, and in their operation, may be made by those skilled in the art without departing from the spirit of the invention. For example, it is expressly intended that all combinations of those elements which perform substantially the same function in substantially the same way to achieve the same results are within the scope of the invention. Moreover, it should be recognized that structures and/or elements shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

What is claimed is:

1. A surgical instrument, comprising:
   a hollow shank having a proximal end and a distal end;
   an actuating device arranged at said proximal end of said hollow shank and movable in a first actuating movement direction;
   an instrument tip arranged at the distal end of said hollow shank, said instrument tip being pivotably connected relative to said hollow shank by a pivoting axis so that said instrument tip is pivotable about the pivoting axis toward said hollow shank;
   a mouth part having a longitudinal axis and rotatably arranged on the instrument tip such that said mouth part is rotatable relative to said instrument tip about said longitudinal axis; and
   a gear mechanism connected between said actuating device and said instrument tip for rotating said mouth part in response to a movement of said actuating device in the first actuating movement direction in accordance with a first transmission ratio, wherein said first actuating movement is in response to an operator movement of said actuating device, wherein
   said actuation device comprises a handle having a grip end fixed thereto and a trigger relatively moveably connected to said handle, and said actuation device further comprising a joint mechanism formed at the proximal end of said hollow shank, wherein said grip end is twistably and swivelably connected to said hollow shank by said joint mechanism such that said grip end is twistable about a twisting axis and swivelable about a swivelling axis that is separate from said from said twisting axis.

2. The surgical instrument of claim 1, wherein said instrument tip includes a seat supported on the distal end of said hollow shank such that said seat is fixed with respect to rotation relative to said hollow shank and is pivotal relative to said hollow shank about a seat pivot point, said mouth part being supported on said seat so that said mouth part rotatable relative to said seat.

3. The surgical instrument of claim 2, wherein said actuating device is movable in a second actuating movement direction, said gear mechanism transforming the second actuating movement of said actuating device into a pivoting movement of said seat relative to said hollow shank, the pivoting movement being in accordance with a second transmission ratio in relation to the second actuating movement.

4. The surgical instrument claim 3, wherein said handle is supported at a link point at said joint mechanism, said surgical instrument further comprising a seat actuating rod connected directly to said handle at a predetermined distance from said link point at said joint mechanism, said seat actuating rod passing through said hollow shank and connected to said seat for transmitting a swivel movement of said handle into a pivoting of said seat about said seat pivot point at said distal end of said hollow shank.

5. The surgical instrument of claim 3, wherein said first actuating movement is in response to a manual rotation movement by an operator of the actuation device and said second actuating movement is in response to a bending of a hand by the operator of the actuating device.

6. The surgical instrument of claim 1, said trigger being actuatable independently of the relative position of said actuating device to said hollow shank, said trigger being operatively connected with said mouth part for a decoupled opening and closing of said mouth part in response to a movement of said trigger relative to said actuating device.

7. The surgical instrument of claim 6, wherein said gear mechanism comprises a torsion-resistant flexible shaft supported in said hollow shank and connected to said mouth part for transmitting a moment of rotation to said mouth part for rotating said mouth part in said seat, and an actuating pull guided inside of said flexible shaft, said actuating element being operatively connected to said actuating pull.

8. The surgical instrument of claim 6, wherein said first actuating movement is in response to a manual rotation movement by an operator of the actuation device and said second actuating movement is in response to a bending of a hand by the operator of the actuating device.

9. The surgical instrument of claim 1, wherein said gear mechanism comprises a torsion-resistant flexible shaft supported in said hollow shank and connected to said mouth part for transmitting a moment of rotation to said mouth part for rotating said mouth part in said seat.

10. The surgical instrument of claim 9, wherein a portion of said torsion-resistant flexible shaft comprises a gearwheel section, said gear mechanism further comprising a further gearwheel in meshed engagement with said gearwheel section of said torsion resistant flexible shaft, said actuating device being operatively connected to said further gear wheel for driving said further gearwheel.

11. The surgical instrument according to claim 10, wherein said proximal end of said hollow shank comprises a bearing, said joint mechanism comprising a hollow one of a wheel and sleeve rotatably accommodated in said bearing of said hollow shank and forming said further gearwheel, said hollow one of a wheel and sleeve enclosing said gearwheel section of said shaft and forming a bearing head for swivelably linking said handle to said hollow shaft.

12. The surgical instrument of claim 1, wherein said first actuating movement is in response to a manual rotation movement by an operator of the actuation device.

13. The surgical instrument of claim 1, wherein said bendable instrument tip includes a seat which is swivelable relative to said hollow shank, said activating device being movable in a second actuating movement direction, said gear mechanism transforming the second actuating movement of said actuating device into a swiveling of said seat relative to said hollow shank, and the swiveling movement being in accordance with a second transmission ratio in relation to the second actuating movement.

14. A surgical instrument, comprising:
a hollow shank having a proximal end and a distal end;
an actuating device arranged at said proximal end of said hollow shank and movable in a first actuating movement direction;
an instrument tip arranged at the distal end of said hollow shank, said instrument tip being pivotably connected relative to said hollow shank by a pivoting axis so that said instrument tip is pivotable about the pivoting axis toward said hollow shank;
a mouth part having a longitudinal axis and rotatably arranged on the instrument tip such that said mouth part is rotatable relative to said instrument tip about said longitudinal axis;
a gear mechanism connected between said actuating device and said instrument tip for rotating said mouth part in response to a movement of said actuating device in the first actuating movement direction in accordance with a first transmission ratio, wherein said first actuating movement is in response to an operator movement of said actuating device;
an actuating element movably connected to said actuating device, said actuating element being actuatable independently of the relative position of said actuating device to said hollow shank, said actuating element being operatively connected with said mouth part for a decoupled opening and closing of said mouth part in response to a movement of said actuating element relative to said actuating device, wherein said gear mechanism comprises a torsion-resistant flexible shaft supported in said hollow shank and connected to said mouth part for transmitting a moment of rotation to said mouth part for rotating said mouth part in said seat, and an actuating pull guided inside of said flexible shaft, said actuating element being operatively connected to said actuating pull; and
an eccentric rod connected to said actuating element, first and second pinions in meshed engagement arranged on said bearing head, the eccentric rod being adapted to drive the first and second pinions, an elongation rod eccentrically supported on said second pinion, a rocker arm arranged at said proximal end of said hollow shank and to which said mouth part actuating pull is connected such that the movement of said elongation rod is deflected by said rocker arm into a movement of said mouth part actuating pull.

* * * * *